(12) United States Patent
Yeo

(10) Patent No.: US 8,871,228 B2
(45) Date of Patent: Oct. 28, 2014

(54) INJECTABLE COMPOSITION CONTAINING HYDROXYCHLOROQUINE FOR LOCAL ADMINISTRATION FOR TREATING HEMORRHOIDS

(76) Inventor: Oh-Young Yeo, Goyang-si (KR)

( * ) Notice: Subject to any disclaimer, the term of this patent is extended or adjusted under 35 U.S.C. 154(b) by 0 days.

(21) Appl. No.: 13/379,626

(22) PCT Filed: Jun. 18, 2010

(86) PCT No.: PCT/KR2010/003937
§ 371 (c)(1),
(2), (4) Date: Dec. 20, 2011

(87) PCT Pub. No.: WO2010/151004
PCT Pub. Date: Dec. 29, 2010

(65) Prior Publication Data
US 2012/0108633 A1  May 3, 2012

(30) Foreign Application Priority Data

Jun. 23, 2009  (KR) .................. 10-2009-0055860

(51) Int. Cl.
| | | |
|---|---|---|
| A61K 35/14 | (2006.01) | |
| A61K 35/12 | (2006.01) | |
| A61K 31/44 | (2006.01) | |
| A61K 9/00 | (2006.01) | |
| A61K 45/06 | (2006.01) | |
| A61K 31/4706 | (2006.01) | |

(52) U.S. Cl.
CPC .............. *A61K 9/0019* (2013.01); *A61K 31/44* (2013.01); *A61K 45/06* (2013.01); *A61K 31/4706* (2013.01); *A61K 9/0031* (2013.01)
USPC ................. 424/400; 424/93; 435/2; 514/313; 546/163

(58) Field of Classification Search
CPC ........................... A61K 9/0019; A61K 9/0031
USPC ........... 424/400, 532, 93, 72; 435/2; 514/313; 546/163
See application file for complete search history.

(56) References Cited

U.S. PATENT DOCUMENTS

| | | | |
|---|---|---|---|
| 6,127,111 A | * | 10/2000 | Braun .............................. 435/2 |
| 2005/0090553 A1 | * | 4/2005 | Shapiro ....................... 514/565 |
| 2006/0079492 A1 | * | 4/2006 | Ahlem et al. ................ 514/178 |

FOREIGN PATENT DOCUMENTS

KR  1020020040767 A1  5/2002

OTHER PUBLICATIONS

Clark, P. et al., Hydroxychloroquine Compared with Placebo in Pheumatoid Arthritis. Annals of Internal Medicine. 1993, 119(11), pp. 1067-1071.
O'Dell, J. R. et al., Treatment of Rhenumatoid Arthritis with Methotrexate alone, Sulfasalzine and Hydroxychloroquine, or a Combination of All Three Medications. The New England Journal of Medicine. 1996, 334(20), pp. 1287-1291.
Raoult, D. et al., Treatment of Q Fever Endocarditis. Archives of Internal Medicine. 1999, vol. 159, pp. 167-173.

* cited by examiner

*Primary Examiner* — Johann R Richter
*Assistant Examiner* — Yanzhi Zhang
(74) *Attorney, Agent, or Firm* — Sherr & Jiang, PLLC

(57) ABSTRACT

The present invention relates to an injectable composition for local administration for treating hemorrhoids, which contains hydroxychloroquine. Specifically, the composition contains a solution of hydroxychloroquine in physiological saline for injection, together with a local anesthetic and an antioxidant.

9 Claims, 8 Drawing Sheets

INJECTABLE COMPOSITION CONTAINING HYDROXYCHLOROQUINE FOR LOCAL ADMINISTRATION FOR TREATING HEMORRHOIDS

BACKGROUND OF THE INVENTION

1. Technical Field

The present invention relates, in general, to an injectable composition for local administration for treating hemorrhoids, which contains hydroxychloroquine, and more particularly to an injectable composition for treating hemorrhoids, which is to be injected directly into the hemorrhoidal area to harden the hemorrhoidal tissue so as to block metabolism in the hemorrhoidal tissue, thereby inactivating the hemorrhoidal tissue, and ultimately necrotizing the hemorrhoidal tissue.

2. Description of the Related Art

Hemorrhoids are the first leading cause of hospitalization in Korea, and 50% or more of people in their 50s or older suffer from these diseases (the Seoul National University Hospital). Also, about 50 of the USA population suffers from these diseases.

Generally, hemorrhoidal diseases which are the so-called hemorrhoids include hemorrhoids, anal fissure, perianal tumors, anal fistula, and show major symptoms, including bleeding, prolapse, pain, itching, rectal dysfunction, and soiling. Among them, the term "hemorrhoids" is most frequently used.

Hemorrhoids occur due to the stretching and expansion of vascular tissue beneath the skin and mucus tissue of the anal and are masses caused by stretching of the skin and mucosa covering the anal blood vessels. Hemorrhoids are classified into internal hemorrhoids, external hemorrhoids, and mixed hemorrhoids. Hemorrhoids occurring above the dentate line (approximately 1.5 cm above the inner verge of the anus dilator) are referred to as internal hemorrhoids; hemorrhoids occurring below the dentate line are referred to as external hemorrhoids; and hemorrhoids occurring both above and below the dentate line are referred to as mixed hemorrhoids. In the initial stage, there are only internal or external hemorrhoids, but in many cases, the internal or external hemorrhoids progress to mixed hemorrhoids with the passage of time.

The degree of progression of internal hemorrhoids is divided according to the degree of protrusion of hemorrhoids from the anus into: stage 1 in which a hemorrhoid is diagnosed due to bleeding, but the hemorrhoid does not protrude from the anus; stage 2 in which the hemorrhoid protrudes during bowel evacuation, but it returns to its original position immediately after bowel evacuation; stage 3 in which the hemorrhoid protrudes during bowel evacuation, and the protruded hemorrhoid returns to its original position a significant amount of time after bowel evacuation or returns by thrusting or lying down; and stage 4 in which the hemorrhoid that protruded during bowel evacuation does not easily returns to its original position or protrudes again immediately after return to its original position.

The degree of progression of external hemorrhoids is not objectively divided or can be divided based on the period of occurrence of thrombosis in view of the balance with internal hemorrhoids. Specifically, a stage-1 external hemorrhoid is referred to when thrombosis occurs and is swollen for less than 10 days per year; a stage-2 external hemorrhoid is referred to when thrombosis occurs and is swollen for about 11-20 days per year; a stage-3 external hemorrhoid is referred to when thrombosis occurs and is swollen for more than 3 weeks per year; and a stage-4 external hemorrhoid is referred to when thrombosis frequently occurs.

General methods for treating such hemorrhoids include: a method of suppressing bleeding of internal hemorrhoids; a method of suppressing thrombosis in external hemorrhoids and the resulting edema and pain; administration of internal medicines or suppositories; and sitz bath.

Internal medicines for treating hemorrhoids are based on blood circulation-improving agents and include about 10 commercially available medicinal products. Suppositories for treating hemorrhoids are composed of components having pain-killing, anti-inflammatory, antibacterial and astringent effects and include about 20 commercially available medicinal products.

As ointments and suppositories for treating hemorrhoids, formulations containing local anesthetics, steroidal agents and antihistamine agents are mainly used. Administration of the local anesthetics or steroidal agents alleviates temporary discomfort, but it delays wound healing and is highly likely to cause a variety of systemic and local side effects. Furthermore, administration of non-steroidal anti-inflammatory agents around a wound is prohibited, because it delays the treatment of disease.

In addition, surgical methods are avoided by patients and frequently fail to remove the root of hemorrhoids, because these methods remove only the protruding portion of hemorrhoids.

Korean Patent Laid-Open Publication No. 10-2005-0102663 discloses an agent for external application for treating hemorrhoids and anal fissure, which comprises acetylsalicylic acid or its salt as an active ingredient.

Korean Patent Registration No. 10-0863758 discloses a pharmaceutical composition for local application for treating acute or chronic anal fissure, thrombotic internal or external hemorrhoids and hemorrhoidal diseases, the composition containing an adenosine receptor antagonist selected from the group consisting of theophylline and dyphylline.

Korean Patent Laid-Open Publication No. 10-2008-0105857 discloses a composition for direct local application to surfaces, the composition containing a swellfish spawn extract, a swellfish liver extract, egg yolk oil and a *Cnidium Rhizome* extract and having activity of treating anal and rectal diseases.

However, an injectable composition for treating hemorrhoids containing hydroxychloroquine as disclosed in the present invention is not yet known, which is to be injected directly into the affected area to harden the hemorrhoidal tissue so as to block metabolism in the hemorrhoidal tissue, thereby inactivating the hemorrhoidal tissue, and ultimately necrotizing the hemorrhoidal tissue.

SUMMARY OF THE INVENTION

The present invention provides an injectable composition for local administration for treating hemorrhoids, which contains hydroxychloroquine. When the composition of the present invention is administered directly into the affected area such that it penetrates into the root of hemorrhoids to necrotize the tissue cells of the hemorrhoids, the affected tissue will shrink to about ⅓ of the original size and, as a result, exfoliate.

With respect to the mechanism of action of the present invention, when the injectable composition for local administration for treating hemorrhoids containing hydroxychloroquine according to the present invention is administered directly into the affected area, it will harden the affected tissue to block metabolism therein, and ultimately inactivate the affected tissue to necrotize the affected tissue.

DETAILED DESCRIPTION OF THE INVENTION

Figure 1:
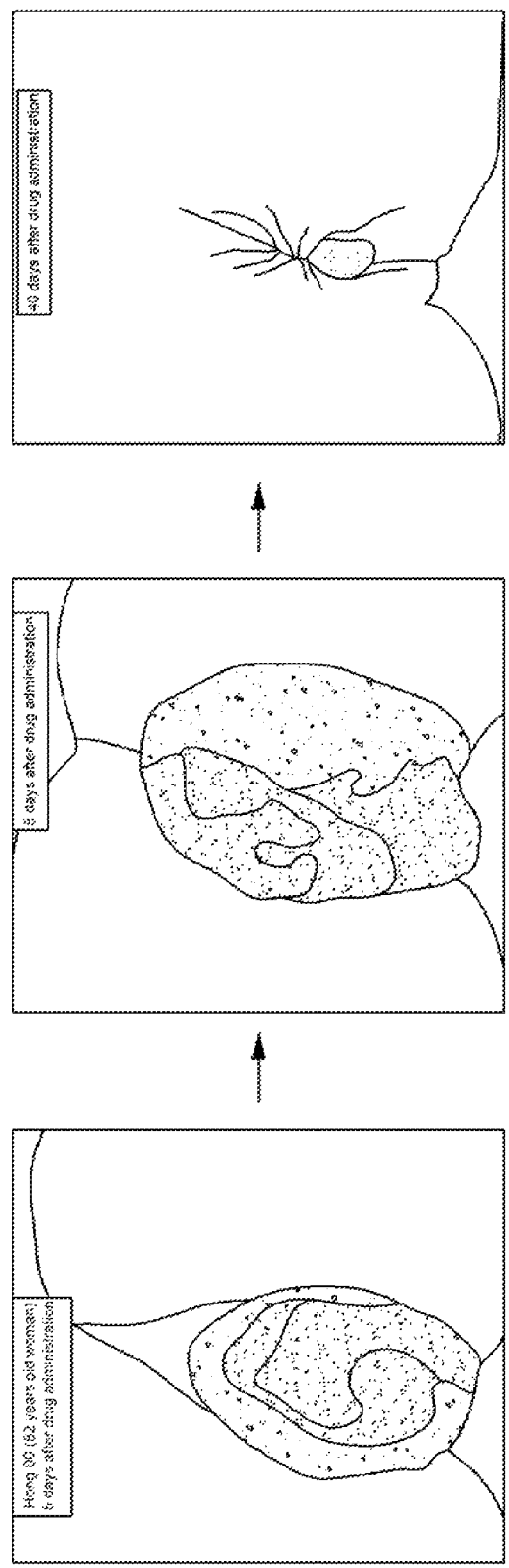
FIG. 1 is a set of photographs showing the affected area of Hong 00 (82 years old woman) 5, 8 and 40 days after local administration of the composition of the present invention.

The present invention relates to an injectable composition for local administration for treating hemorrhoids, which contains hydroxychloroquine. Specifically, the present invention relates to an injectable composition for local administration, which contains 5-10 g of hydroxychloroquine dissolved in 10 ml of physiological saline for injection, together with a local anesthetic and an antioxidant.

In the composition of the present invention, the hydroxychloroquine is preferably contained in an amount of 1-60% w/v, and more preferably 50% w/v, based on the volume of the physiological saline for injection.

In the present invention, when hydroxychloroquine is added to physiological saline for injection in an amount of 50% w/v, it will not be easily dissolved, and thus will be present in a suspension. In this case, it is preferably used after dissolution in hot water.

If the content of hydroxychloroquine relative to physiological saline for injection is less than 1% w/v, the desired therapeutic effect will not be obtained, and if the content is more than 60% w/v, hydroxychloroquine will not be easily dissolved, thus making it difficult to formulate, and the necrosis of tissue can rapidly occur, thus causing undesired results.

The local anesthetic that is used in the present invention serves to remove pain when the composition is administered by injection directly into the affected area. As the local anesthetic, lidocaine is preferably contained in an amount of 1-2% w/v.

The antioxidant that is used in the present invention serves to stabilize the composition. As the antioxidant, riboflavin is contained in an amount of 0.1% w/v.

The injectable composition for local administration may be prepared using the above-described formulation according to any conventional method known in the art.

For treatment of hemorrhoids, the composition of the present invention is administered by injection directly into the affected area. Preferably, the composition of the present invention is administered 2-3 times at 3-4-day intervals depending on patient's conditions.

When the hemorrhoids of a patient are large in size and cause severe pain, the composition of the present invention may be administered in small amounts daily for one week or more.

Hereinafter, the present invention will be described in detail with reference to examples and test examples.

Example 1

Preparation of Injectable Composition for Local Administration According to the Present Invention (Hereinafter Referred to as "Haemsol 50")

10 g hydroxychloroquine was dissolved in 10 ml of saline for injection, and 20 w/v of lidocaine and 0.1% w/v of riboflavin were added thereto, thereby preparing an injectable composition for local administration (Haemsol 50).

Administration into Hemorrhoids 0.2-0.3 ml of the Haemsol 50 solution was administered 2-3 times at 3-4-day intervals with a focus on the apex of hemorrhoids regarded as triangular pyramids.

Test Example 1

Hong 00 (82 years old woman)
She has suffered from a hemorrhoid for 60 years and received various treatments. Removal of her hemorrhoid by surgery was impossible, because the hemorrhoid was too large in size and she was too old to receive surgery.

Before administration of the Haemsol 50 solution, the hemorrhoid had a size of 3.5×5.0 cm and caused severe pain.

1.2 ml of the Haemsol 50 solution was extensively administered, and after 4 days, the Haemsol 50 solution was administered again.

8 days after the administration of the Haemsol 50 solution, the size of the hemorrhoid increased to 4.5×6.5 cm, and the pain was reduced.

The affected tissue started to necrotize from 14 days after administration of the Haemsol 50 solution.

21 days after administration, the hemorrhoid was completely exfoliated and necrotized, and the necrotized tissue was applied with Silvadine cream.

Treatment for the regeneration of tissue and the prevention of inflammation was performed, and the tissue was completely regenerated after 36 days of administration (see FIG. 1).

Test Example 2

Kim 00 (36 years old woman)
She has suffered from bleeding and hemorrhoid for a long period of time such that it was inconvenient to evacuate the bowels.

Before administration of the Haemsol 50 solution, she had an upper hemorrhoid having a diameter of 1.5×1.0 cm and a lower hemorrhoid having a diameter of 2.0×1.0 cm. After the first administration of the Haemsol 50 solution, the hemorrhoids became slightly larger.

14 days after administration, the hemorrhoid was necrotized, completely exfoliated and had large holes formed therein.

Figure 2:
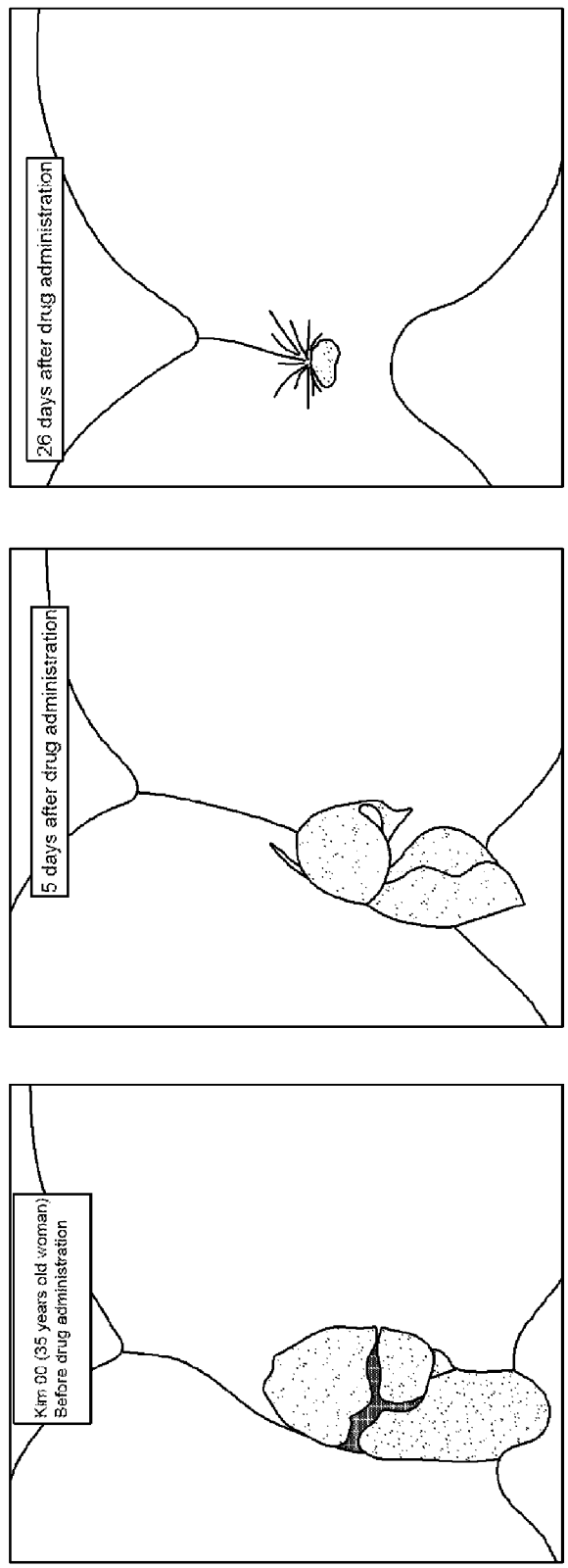
FIG. 2 is a set of photographs showing the affected area of Kim 00 (36 years old woman) before and 5, and 26 days after local administration of the composition of the present invention.

Silvadine cream was applied to the affected area to prevent inflammation, and treatment for tissue regeneration was performed. 26 days after administration, the tissue was completely regenerated (see FIG. 2).

Test Example 3

Figure 3:
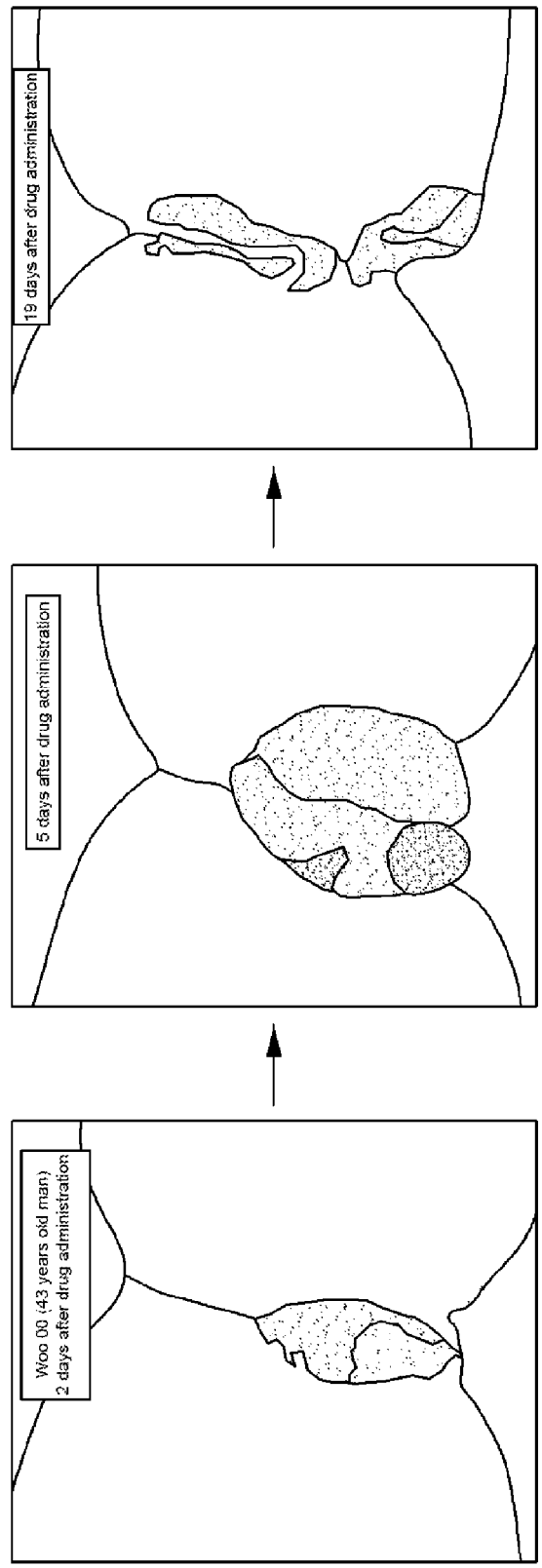
FIG. 3 is a set of photographs showing the affected area of Woo 00 (43 years old man) 2, 5 and 19 days after local administration of the composition of the present invention.

Woo 00 (43 years old man)
Before administration of the Haemsol 50 solution, the hemorrhoid was regarded to have a size of 1.0×2.0 cm. 5 days after the first administration of the Haemsol 50 solution, a latent hemorrhoid having a size of 3.5×5.0 cm appeared. 19 days after second administration, the hemorrhoid was completely necrotized and exfoliated. The necrotized tissue was applied with Silvadine cream, and the tissue was completely regenerated 30 days after administration of the Haemsol 50 solution (FIG. 3).

Test Example 4

Figure 4:
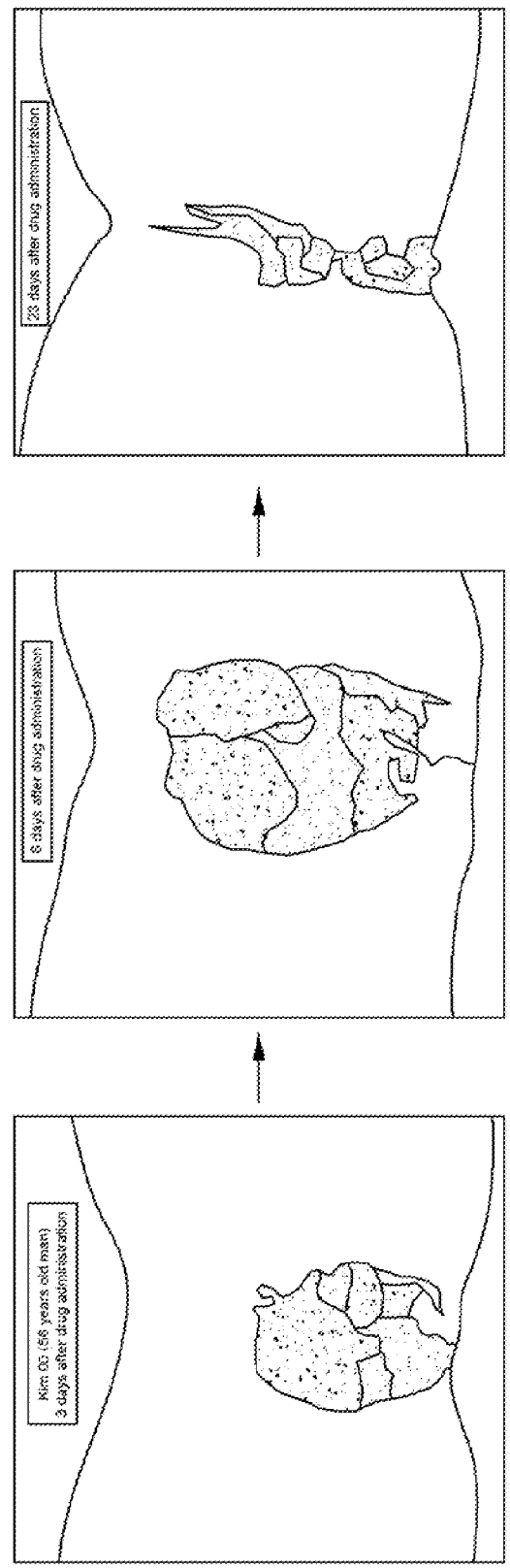
FIG. 4 is a set of photographs showing the affected area of Kim 00 (56 years old man) 3, 6 and 23 days after local administration of the composition of the present invention.

Kim 00 (56 years old man)
He has suffered from a hemorrhoid, even though he received treatments for long period of time.
Before administration of the Haemsol 50 solution, the size of the hemorrhoid was 2.0×2.5 cm. It became gradually larger after the first administration of the Haemsol 50 solution, and it reached 3.5×4.5 cm at day 6 after administration. 23 days after administration, the hemorrhoid was completely exfoliated.
Silvadine cream was applied to the affected area for about 2 weeks, and then the tissue was completely regenerated (see FIG. 4).

Test Example 5

Figure 5:
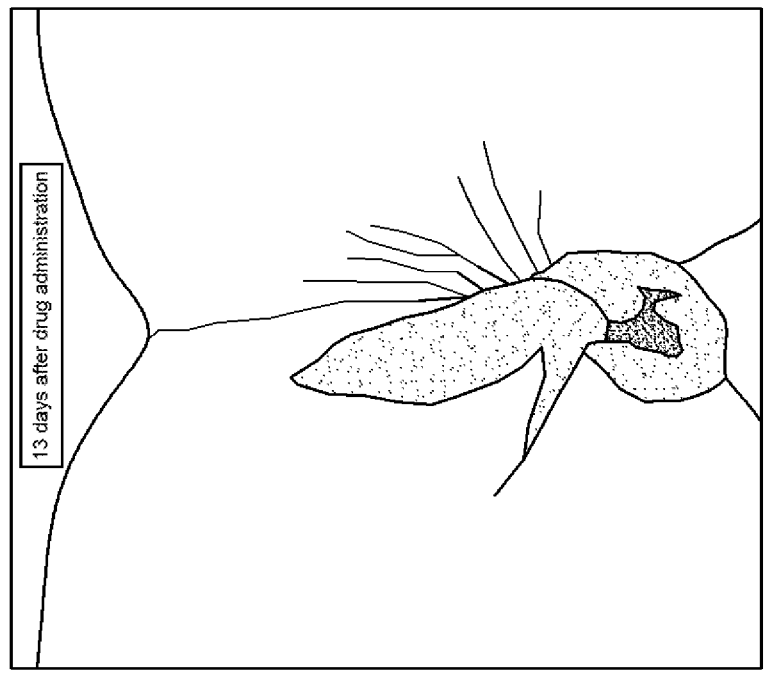
FIG. 5 is a set of photographs showing the affected area of Kim 00 (42 years old woman) 4 and 13 days after local administration of the composition of the present invention.
Figure 5:
Figure 5:
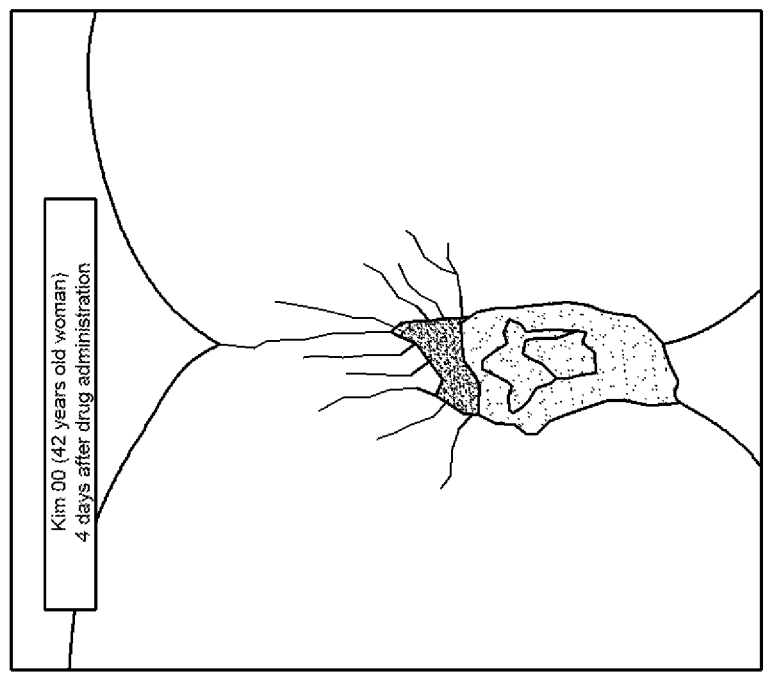

Kim 00 (42 years old woman)
He has suffered from a hemorrhoid and bleeding for several years.
Before administration of the Haemsol 50 solution, the size of the hemorrhoid was 2.5×3.0 cm. 3 days after administration of the Haemsol 50 solution, the hemorrhoid size increased to 3.0×4.0 cm.
13 days after administration of the Haemsol 50 solution, the hemorrhoid was completely necrotized.
Silvadine cream was applied to the affected area, and the tissue was completely regenerated 2 weeks after administration of Haemsol 50 solution (see FIG. 5).

Test Example 6

Figure 6:
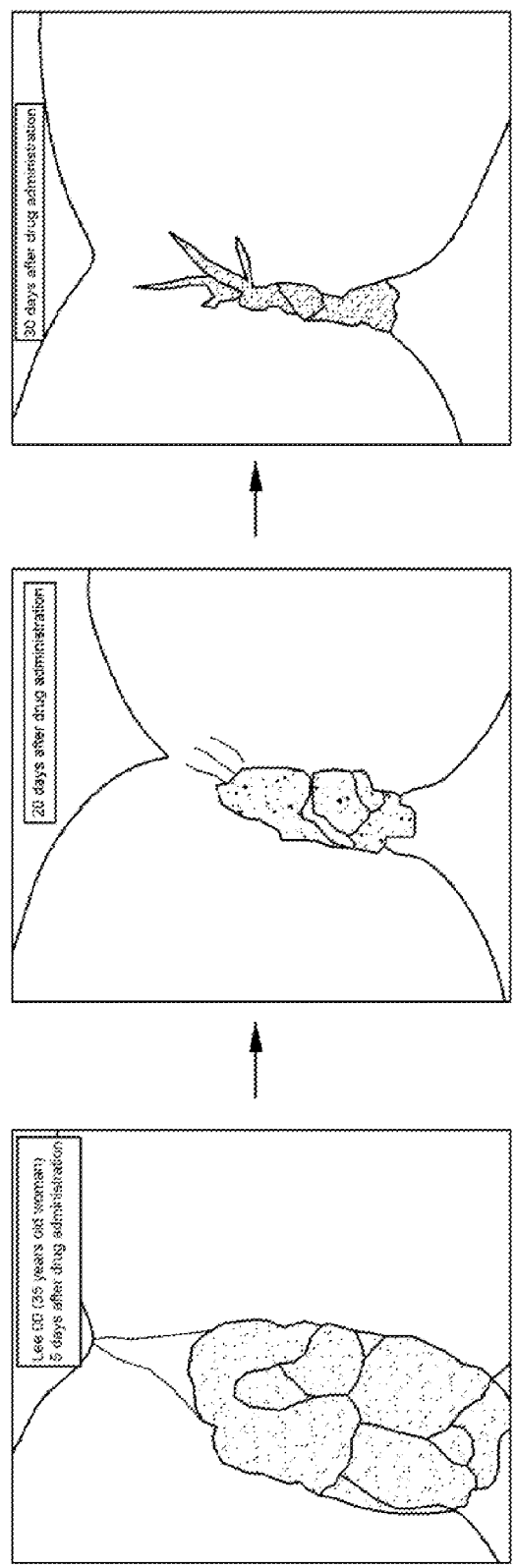
FIG. 6 is a set of photographs showing the affected area of Lee 00 (35 years old woman) 5, 20 and 30 days after local administration of the composition of the present invention.

Lee 00 (35 years old woman)
He underwent surgery after suffered from a hemorrhoid for several years. The hemorrhoid recurred after surgery and developed like a bundle of grapes (large hemorrhoid differentiated into about 4 parts).
5 days after administration of the Haemsol 50 solution, the hemorrhoid increased to a size of 3.5×5.0 cm.
21 days after administration of the Haemsol 50 solution, the hemorrhoid was necrotized and completely separated.
Silvadine cream was applied to the affected area, and the tissue was completely regenerated 31 days after administration of Haemsol 50 solution (see FIG. 6).

Test Example 7

Cho 00 (36 years old man)
He has suffered from a hemorrhoid for a long period of time.

Figure 7:
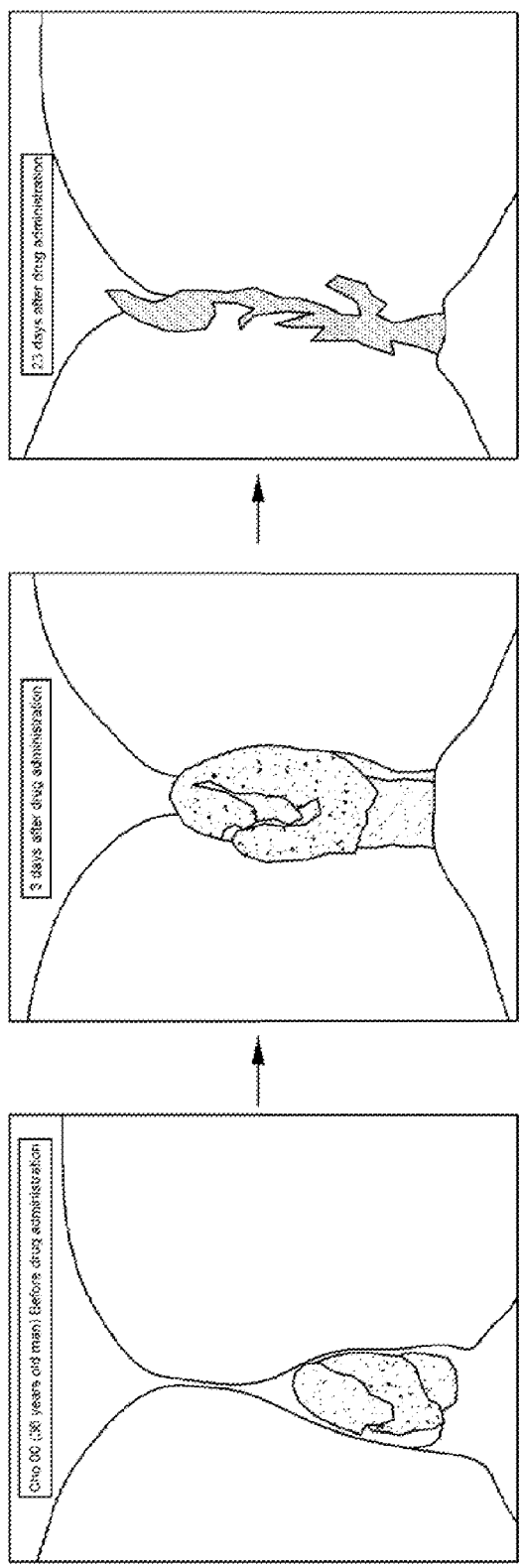
FIG. 7 is a set of photographs showing the affected area of Cho 00 (36 years old man) before and 3 and 23 days after local administration of the composition of the present invention.

Before administration of the Haemsol 50 solution, the size of the hemorrhoid was 1.5×2.0 cm.
3 days after administration of the Haemsol 50 solution, the size of the hemorrhoid increased to 2.5×3.0 cm.
23 days after administration of the Haemsol 50 solution, the hemorrhoid was necrotized and completely separated.
The tissue was completely regenerated 30 days of the Haemsol 50 solution (see FIG. 7).

Test Example 8

Figure 8:
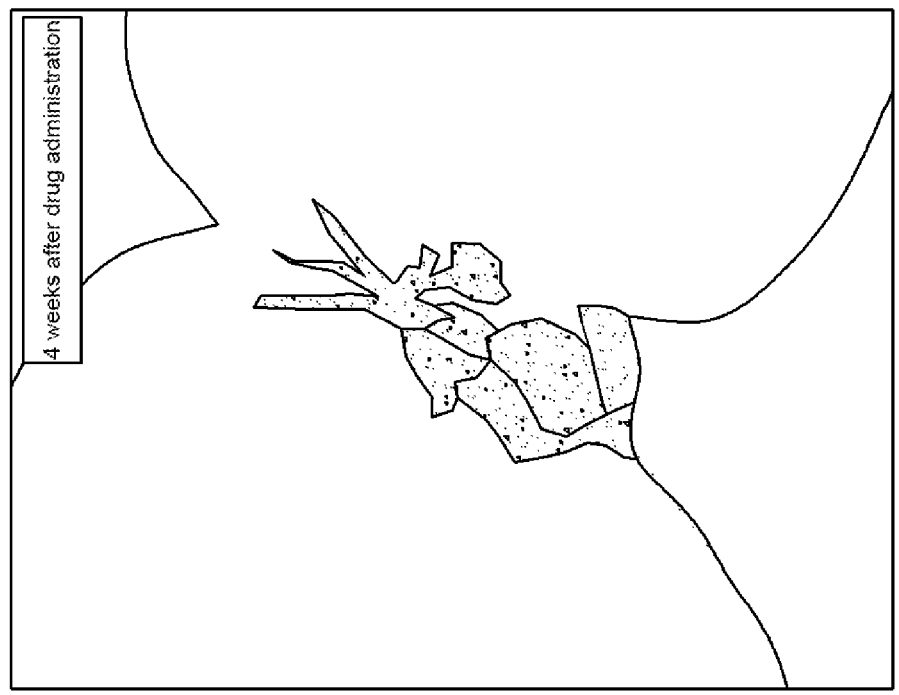
FIG. 8 is a set of photographs showing the affected area of Lee 00 (51 years old woman) before and 4 weeks after local administration of the composition of the present invention.
Figure 8:
Figure 8:
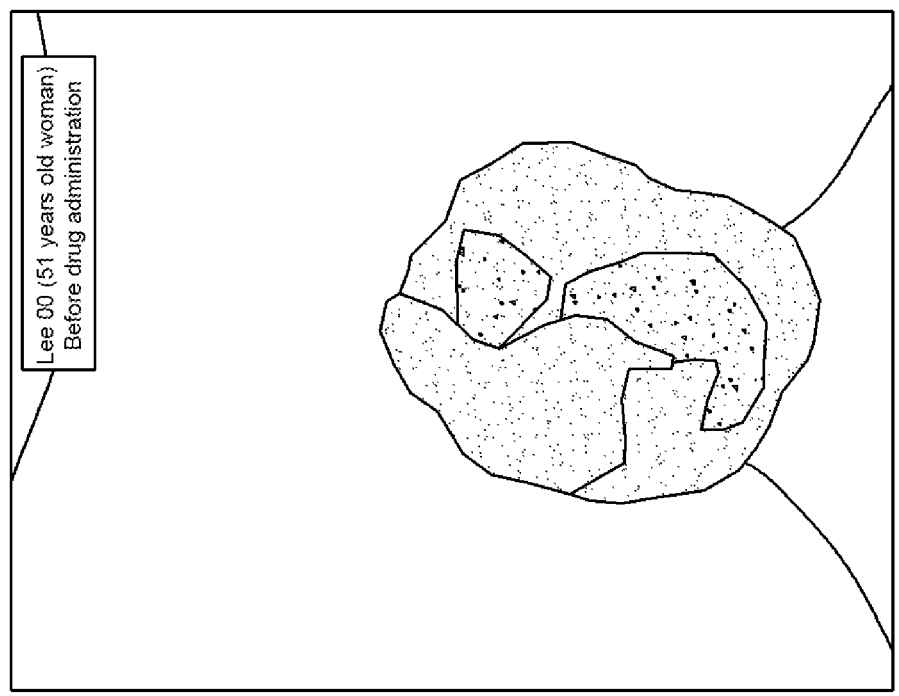

Lee 00 (51 years old woman)
She has suffered from a large hemorrhoid such that it was inconvenient to evacuate the bowels.
Before administration of the Haemsol 50 solution, the size of the hemorrhoid was 3.5×5.0 cm.
From 10 days after of the Haemsol 50 solution, the hemorrhoid started to necrotize and exfoliate.
16 days after administration of the Haemsol 50 solution, the hemorrhoid was completely necrotized and exfoliated. 6 weeks after administration of the Haemsol 50 solution, the tissue was completely regenerated (see FIG. 8).

As described above, the present invention provides an injectable composition for local administration for treating hemorrhoids containing hydroxychloroquine. When the composition of the present invention is administered directly into the affected area such that it penetrates into the root of hemorrhoids to necrotize the tissue cells of the hemorrhoids, the affected tissue will shrink to about ⅓ of the original size and, as a result, exfoliate. Thus, the composition of the present invention makes it possible to treat hemorrhoids in a simple and fundamental manner without performing a surgical operation.

The invention claimed is:
1. An injectable composition for local administration for treating hemorrhoids, which contains hydroxychloroquine in an amount of 40-60% w/v 10 ml of physiological saline for injection.
2. The injectable composition of claim 1, wherein the hydroxychloroquine is contained in an amount of 50% w/v 10 ml of physiological saline for injection.
3. The injectable composition of as in claim 1 or 2, wherein the composition further contains a local anesthetic and an antioxidant.
4. The injectable composition of claim 3, wherein the local anesthetic is lidocaine which is contained in an amount of 2% w/v, and the antioxidant is riboflavin which is contained in an amount of 1% w/v.
5. A method for treating hemorrhoids, comprising:
preparing an injectable composition which contains hydroxychloroquine in an amount of 1-60% w/v; and
injecting the composition directly into a hemorrhoid of a subject.
6. The method of claim 5, wherein the hydroxychloroquine is contained in an amount of 50% w/v.
7. The method of claim 5, wherein the composition further contains a local anesthetic and an antioxidant.
8. The method of claim 7, wherein the local anesthetic is lidocaine which is contained in an amount of 2% w/v, and the antioxidant is riboflavin which is contained in an amount of 1% w/v.
9. The method for treating hemorrhoids of claim 5, wherein the hydroxychloroquine is contained in an amount of 40-60% w/v.

* * * * *